US010010537B2

(12) United States Patent
Motheram et al.

(10) Patent No.: US 10,010,537 B2
(45) Date of Patent: *Jul. 3, 2018

(54) CLEVIDIPINE EMULSION FORMULATIONS CONTAINING ANTIMICROBIAL AGENTS

(75) Inventors: Rajeshwar Motheram, Randolph, NJ (US); Gregory Charles Williams, Bernardsville, NJ (US)

(73) Assignee: Chiesi Farmaceutici S.p.A., Parma (IT)

( * ) Notice: Subject to any disclaimer, the term of this patent is extended or adjusted under 35 U.S.C. 154(b) by 888 days.

This patent is subject to a terminal disclaimer.

(21) Appl. No.: 13/270,004

(22) Filed: Oct. 10, 2011

(65) Prior Publication Data

US 2012/0088804 A1   Apr. 12, 2012

Related U.S. Application Data

(60) Provisional application No. 61/392,294, filed on Oct. 12, 2010.

(51) Int. Cl.
*A61K 31/198* (2006.01)
*A61K 31/685* (2006.01)
*A61K 31/4418* (2006.01)
*A61K 31/4422* (2006.01)
*A61K 45/06* (2006.01)
*A61K 47/10* (2017.01)
*A61K 47/44* (2017.01)
*A61K 9/00* (2006.01)
*A61K 47/24* (2006.01)
*A61K 9/107* (2006.01)
*A61K 47/12* (2006.01)
*A61K 47/18* (2017.01)
*A61K 47/22* (2006.01)

(52) U.S. Cl.
CPC ........ *A61K 31/4418* (2013.01); *A61K 9/0019* (2013.01); *A61K 9/107* (2013.01); *A61K 45/06* (2013.01); *A61K 47/10* (2013.01); *A61K 47/12* (2013.01); *A61K 47/183* (2013.01); *A61K 47/22* (2013.01); *A61K 47/24* (2013.01); *A61K 47/44* (2013.01)

(58) Field of Classification Search
CPC ................ A61K 31/198; A61K 31/685; A61K 31/4418; A61K 31/4422
See application file for complete search history.

(56) References Cited

U.S. PATENT DOCUMENTS

| 5,714,520 | A | 2/1998 | Jones et al. | |
|---|---|---|---|---|
| 5,739,152 | A * | 4/1998 | Andersson et al. | 514/356 |
| 5,856,346 | A | 1/1999 | Andersson et al. | |
| 6,350,877 | B1 | 2/2002 | Mattson et al. | |
| 8,148,346 | B2 | 4/2012 | Banchereau et al. | |
| 2005/0186230 | A1 * | 8/2005 | Chen | A61K 9/0019 424/400 |
| 2006/0094699 | A1 | 5/2006 | Kampen et al. | |
| 2006/0104913 | A1 | 5/2006 | Chaudry | |
| 2008/0206170 | A1 | 8/2008 | Nivaggioli et al. | |
| 2008/0305147 | A1 | 12/2008 | Macdonald et al. | |
| 2010/0105743 | A1 | 4/2010 | Krishna et al. | |
| 2010/0113534 | A1 | 5/2010 | Motheram et al. | |
| 2010/0130619 | A1 | 5/2010 | Schwarz et al. | |

FOREIGN PATENT DOCUMENTS

| CN | 101766568 | | 7/2010 |
|---|---|---|---|
| CN | 101780036 | | 7/2010 |
| CN | 101780036 | A | 7/2010 |
| CN | 101791311 | | 8/2010 |
| DE | 4217842 | A1 | 12/1993 |
| DE | 102009003980 | A1 | 7/2010 |
| EP | 0727997 | B1 | 2/2002 |
| EP | 1238677 | A2 | 9/2002 |
| JP | H08506081 | A | 7/1996 |
| JP | 2002502811 | A | 1/2002 |
| JP | 2005521673 | A | 7/2005 |
| JP | 2005538191 | A | 12/2005 |
| JP | 2008501685 | A | 1/2008 |
| JP | 2008503451 | A | 2/2008 |
| JP | 2009512709 | A | 3/2009 |
| JP | 2009534362 | A | 9/2009 |
| JP | 2010505748 | A | 2/2010 |
| JP | 2010100652 | A | 5/2010 |
| JP | 2010531343 | A | 9/2010 |
| JP | 2014504259 | A | 4/2012 |
| KR | 20060026070 | A | 3/2006 |
| WO | 1995013066 | | 5/1995 |
| WO | 1997003669 | A1 | 2/1997 |
| WO | 1998005334 | | 2/1998 |
| WO | 1999066902 | A1 | 12/1999 |
| WO | 2000003736 | A1 | 1/2000 |
| WO | 0189474 | | 11/2001 |
| WO | 2003066024 | A1 | 8/2003 |

(Continued)

OTHER PUBLICATIONS

The International Search Report and Written Opinion by the International Searching Authority, dated Mar. 8, 2012 in the corresponding PCT application No. PCT/US11/55617.
The English translation of the Request for Invalidation in the related Chinese Patent No. 201180048865.x, which was notified by the State Intellectual Property Office on Aug. 21, 2015.
The English translation of the Notice of Opposition in the related European Patent No. 2627173, which was notified by the European Patent Office on Jan. 18, 2016.
D6: Highlights of Prescribing Information for Cleviprex, Jul. 2011.
D7: Extracts from "Handbook of Pharmaceutical Excipients," Pharmaceutical Press, Fourth Edition, 2003.
D9: Press Release Dec. 16, 2009 concerning CleviprexTM, 2009.
D10: Extracts from Bauer, Frömming, Führer, Lehrbuch der Pharmazeutischen Technologie, 7th edition 2002.
D11: FDA letter relating to the change of CleviprexTM prescribing information.

(Continued)

Primary Examiner — Zohreh A Fay

(57) ABSTRACT

Pharmaceutical formulations comprising clevidipine and an antimicrobial agent exhibit a reduced propensity for microbial growth and provide increased convenience to health care workers administering clevidipine-containing formulations to patients.

12 Claims, 1 Drawing Sheet

(56) References Cited

FOREIGN PATENT DOCUMENTS

| WO | 2004010941 A2 | 2/2004 |
| --- | --- | --- |
| WO | 2005120228 A1 | 12/2005 |
| WO | 2005123057 A1 | 12/2005 |
| WO | 2008013785 A2 | 1/2008 |
| WO | 2010014234 | 2/2010 |
| WO | 2010014727 A1 | 2/2010 |
| WO | 2010022259 | 2/2010 |
| WO | 2012051116 | 4/2012 |
| WO | 2012051116 A1 | 4/2012 |

OTHER PUBLICATIONS

Atwood et al., Medscape J. Med 2008, 10(5), 115.

Cleviprex, Package insert, Parsippany, NJ: The Medicines Company; Aug. 2008. The prescribing information for Cleviprex, 2008.

Changa, JAOCS 1983; 60(3): 618-622.

Cranton EM., Chapter 7 in part of Textbook on EDTA Chelation Therapy 2001, 2nd Ed., Hamptom Roads Publishing.

Ebata, H. et al., "Calcium binding to extracellular sites of skeletal muscle calcium channels regulates dihydropyridine binding," Journal of Biological Chemistry, vol. 265, No. 1, Jan. 1990, pp. 177-182.

Han et al. International Journal of Pharmaceutics (2005): 288, pp. 263-271.

Kabara et al., "Preservative-free and self-preserving cosmetics and drugs: principles and practice" 1997; CRC Press, pp. 209-210.

Letter dated Jan. 23, 2008 from Bayer Healthcare.

Letter dated May 14, 2008 from Bayer Healthcare.

Luchowski et al., "Effects of metal cations and calmodulin antagonists on [3H] nitrendipine binding in smooth and cardiac muscle," J. Pharmacol. Exp. Therapeutics, vol. 230, No. 3, pp. 607-613.

Ptasienski et al., "High and low affinity states of the dihydropyridine and phenylalkylamine receptors on the cardiac calcium channel and their interconversion by divalent cations," Biochem Biophys Res. Commun., Jun. 28, 1985 129 (3):910-7.

Press release Dec. 16, 2009 concerning Cleviprex.

Handbook of Pharmaceutical Excipients, 2003, pp. 225-228, 546-548, 560-562.

SmPC SMOF-Lipid, Sep. 23, 2015.

SmPC Propofol Lipuro, Mar. 24, 2017.

SmPC Propofol Fresenius Kabi, Aug. 2016.

SmPC Omegaven, Apr. 23, 2010.

SmPC Lipofundin, Jul. 10, 2014.

SmPC Lipidem, Mar. 2016.

SmPC Clinoleic, Feb. 25, 2015.

SmPC Lipovenos, Jul. 2008.

Hosokawa et al, Formulation Development of a Filter-Sterilizable Lipid Emulsion for Lipophilic KW-3902, a Newly Synthesized Adenosine A1-Receptor Antagonist, Chem. Pharm. Bull., 50 (1) 87-91 (2002).

Han et al., Partition of antimicrobial additives in an intraveinous emulsion and their effect on emulsion physical stability, International Journal of Pharmaceutics, 288 (2005) 263-271.

Excerpt from Bauer, Fromming, Fuhrer, Lehrbuch der pharmazeutischen Technologie, 8th edition 2006.

Letter dated Dec. 29, 2010 from The Medicines Company to the FDA.

Yamaguchi et al., Physicochemical Characterization of Parenteral Lipid Emulsion: Influence of Cosurfactants on Flocculation and Coalescence, Pharmaceutical Research, vol. 12, Mo. 9, 1995.

Fresenius-Kabi-SOP.

Insel et al. Nutrition, 2004, 1, 179-180.

Wasan et al. Role of lipid excipients in modifying oral and parentral drug delivery. 2007: John Wiley and sons; pp. 103-111.

Salunkhe et al. World oilseeds, 1992, p. 12.

Werling et al. Physicochemical stability of phospho-lipid dispersed suspensions of crystalline itraconazole. Eur J. Pharmaceutics and Biopharmaceutics 2008, 69, 1104-1113.

Translation of CN101766568 (Jul. 7, 2010).

Michiaki Yamakage et al. Growth of micro-organisms in two propofol products at room temperature, Journal of the Japan Society for Clinical Anesthesia, Japan, issued in Mar. 2005, vol. 25, No. 2, pp. 154-160 (English-language Abstract included).

Fumiyoshi Ishii, lipid microsphere, journal of japan oil chemist's society., 2000, 49, 10, 1141-1148 (English-language Abstract included).

Yoshiaki Kukida. Studies on influence of edta to bacteria, part 1, influence of EDTA on growth of bacteria, Journal of Okayama Medical Association, Japan, issued in 1959, vol. 71, No. 10-1, pp. 6555-6562 (English-language Abstract included).

Translation of CN101791311 (Aug. 4, 2010).

\* cited by examiner

Clevidipine Degradation Pathway
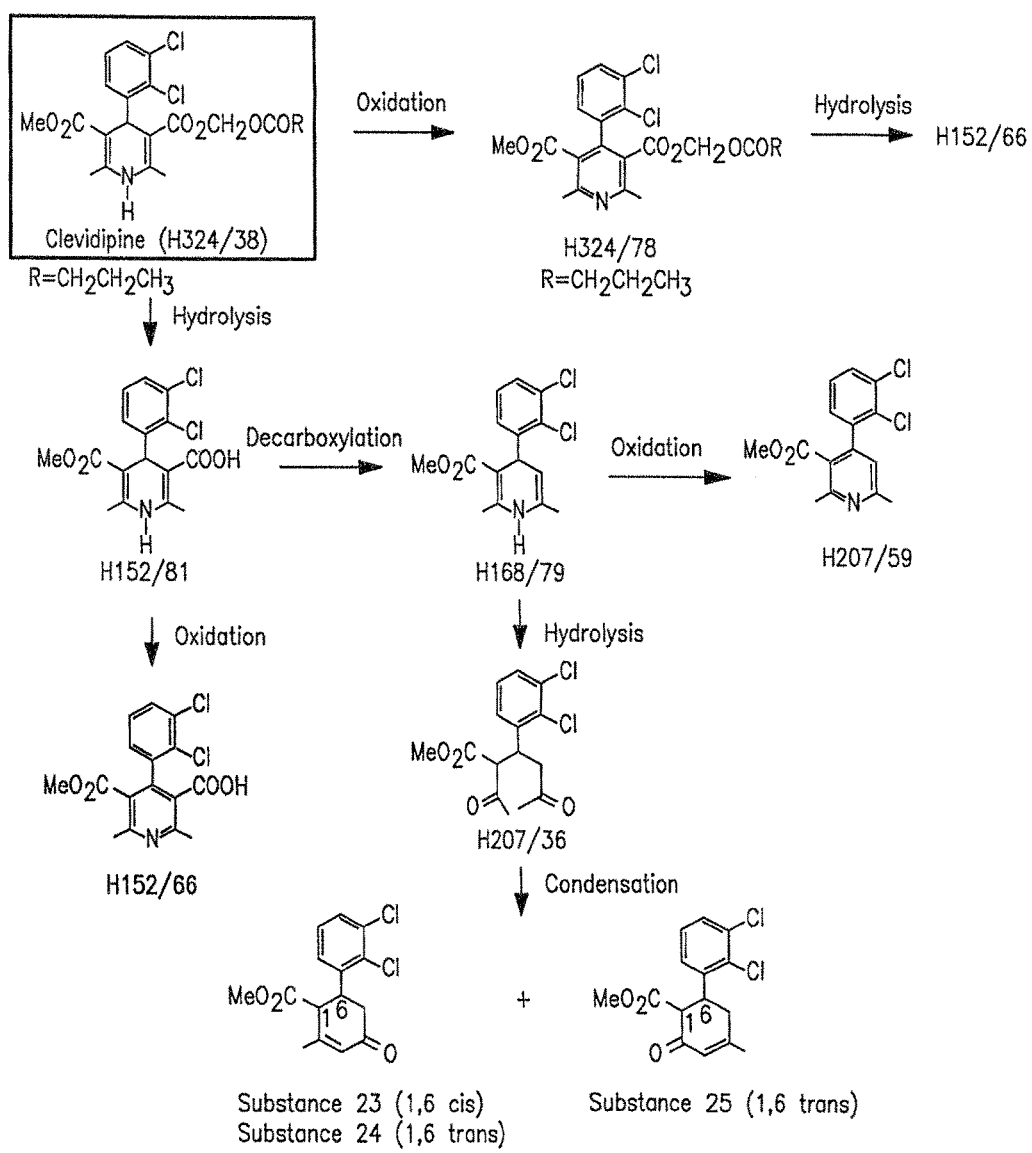

CLEVIDIPINE EMULSION FORMULATIONS CONTAINING ANTIMICROBIAL AGENTS

This application claims priority from U.S. provisional application No. 61/392,294 filed on Oct. 12, 2010. The above referenced application is incorporated by reference herein as if set forth in its entirety.

FIELD OF THE INVENTION

The instant invention relates to a stable, pharmaceutical oil-in-water emulsion formulation for parenteral administration that includes clevidipine and an antimicrobial agent.

BACKGROUND OF THE INVENTION

Clevidipine is a dihydropyridine calcium channel blocker that reduces blood pressure in a subject to which it is administered. It is characterized as a short-acting, highly selective drug that is typically used in a hospital setting due to its rapid metabolism, exhibiting an initial phase half-life of about one minute and a terminal half-life of approximately 15 minutes. More detailed information on short-acting dihydropyridines can be found in U.S. Pat. No. 5,856,346, the entire disclosure of which is incorporated by reference herein as if set forth in its entirety.

Clevidipine is further characterized by having low solubility in water and moderate to high solubility in lipids. When clevidipine is dissolved in oil-in-water emulsions, it results in better solubility and/or less side effects than when other conventional solution formulations are utilized. Cleviprex® is a clevidipine oil-in-water emulsion formulation approved by the U.S. FDA for intravenous administration in the treatment of acute hypertension, primarily in the emergency room and intensive care unit, and in pre-, peri-, and post-operative settings.

Cleviprex® can support microbial growth since it contains soybean oil and egg yolk phospholipids. Therefore, clevidipine oil-in-water emulsion formulations require strict aseptic technique during handling and administration to avoid microbial contamination that can cause infections among patients. To minimize the possibility of microbial contamination, it is recommended that such formulations be discarded four hours after opening. Such a requirement places a burden on health care providers in that fresh vials of the drug must be continually obtained and set up while the patient is being treated. Accordingly; there exists a need for a stable clevidipine emulsion formulation that possesses greater antimicrobial properties, thereby diminishing the risk of microbial contamination in patients and providing greater ease in handling. Such a formulation would also result in cost savings to the health care providers and patients in decreasing the wastage of clevidipine and reducing the time-consuming efforts involved with manipulation and replacement of vials containing the drug.

SUMMARY OF THE INVENTION

Based on the state of the art, it is the object of the present invention to provide a stable clevidipine emulsion formulation with a reduced propensity for microbial contamination.

In a first embodiment of the present invention, there is provided a pharmaceutical formulation comprising clevidipine, or a pharmaceutically acceptable salt or ester thereof, an antimicrobial agent, a lipid, an emulsifier, a tonicity modifier and water.

In one aspect of this embodiment, the present invention provides an oil-in-water emulsion wherein clevidipine is dispersed or dissolved in a lipid, such as soy bean oil, which in turn is emulsified with egg yolk phospholipids in water. The tonicity of emulsion is adjusted with glycerin and further comprises an amount of EDTA sufficient to inhibit growth of microorganisms in the formulation in the event of accidental extrinsic contamination.

In second aspect of this embodiment, the present invention provides an oil-in-water emulsion wherein clevidipine is dispersed or dissolved in a lipid, such as soy bean oil, which in turn is emulsified with egg yolk phospholipids in water. The tonicity of emulsion is adjusted with glycerin and further comprises an amount of EDTA and sodium citrate sufficient to inhibit growth of microorganisms in the formulation in the event of accidental extrinsic contamination.

In a second embodiment of the invention, there is provided a pharmaceutical formulation comprising clevidipine, or a pharmaceutically acceptable salt or ester thereof, an antimicrobial agent, a lipid, an emulsifier, a co-emulsifier, a tonicity modifier and water.

In one aspect of this embodiment, the present invention provides an oil-in-water emulsion wherein clevidipine is dispersed or dissolved in a lipid, such as soy bean oil, which in turn is emulsified with egg yolk phospholipids in water, and wherein the emulsion is further stabilized by the co-emulsifier oleic acid. The tonicity of emulsion is adjusted with glycerin and further comprises an amount of EDTA sufficient to inhibit growth of microorganisms in the formulation.

In a second aspect of this embodiment, the present invention provides an oil-in-water emulsion wherein clevidipine is dispersed or dissolved in a lipid, such as soy bean oil, which in turn is emulsified with egg yolk phospholipids in water, and wherein the emulsion is further stabilized by the co-emulsifier oleic acid. The tonicity of emulsion is adjusted with glycerin and further comprises an amount of EDTA and sodium citrate sufficient to inhibit growth of microorganisms in the formulation in the event of accidental extrinsic contamination.

In a third embodiment of the invention, there is provided a pharmaceutical formulation comprising clevidipine, or a pharmaceutically acceptable salt or ester thereof, an antimicrobial agent, an antioxidant, a lipid, an emulsifier, a tonicity modifier and water.

In one aspect of this embodiment, the present invention provides an oil-in-water emulsion wherein clevidipine is dispersed or dissolved in a lipid, such as soy bean oil, which in turn is emulsified with egg yolk phospholipids in water and stabilized by the antioxidant sodium ascorbate. The tonicity of emulsion is adjusted with glycerin and further comprises an amount of EDTA sufficient to inhibit growth of microorganisms in the formulation.

In a fourth embodiment of the invention, there is provided a pharmaceutical formulation comprising clevidipine, or a pharmaceutically acceptable salt or ester thereof, an antimicrobial agent, an antioxidant, a lipid, an emulsifier, a co-emulsifier, a tonicity modifier and water.

In one aspect of this embodiment, the present invention provides an oil-in-water emulsion wherein clevidipine is dispersed or dissolved in a lipid, such as soy bean oil, which in turn is emulsified with egg yolk phospholipids in water and wherein the emulsion is further physically stabilized by the co-emulsifier oleic acid and chemically stabilized by the antioxidant sodium ascorbate. The tonicity of emulsion is adjusted with glycerin and further comprises an amount of EDTA sufficient to inhibit growth of microorganisms in the formulation.

In aspects of embodiments where the formulation comprises an antioxidant, the antioxidant may reduce the formation of oxidative degradants H324/78 and H152/66

In preferred aspects of each embodiment of the invention, the antimicrobial agent is an alcohol or a chelating agent. More preferably, the antimicrobial agent is disodium edetate (EDTA) or sodium citrate, or both.

In preferred aspects of each embodiment of the invention, the pharmaceutical formulation is sterile. In the event of accidental contamination, the pharmaceutical formulation will retard the growth of microorganisms to no more than 1 log within at least about 24 hours.

In each embodiment of the invention, clevidipine and the emulsion maintain their stability in the formulation. In each embodiment of the invention, the pharmaceutical formulation is for parenteral administration. In each embodiment of the invention, the pharmaceutical formulation will have a pH that ranges from about 6.0 to about 8.8.

BRIEF DESCRIPTION OF THE FIGURES

Understanding of the present invention will be facilitated by consideration of the following detailed description of the embodiments of the present invention taken in conjunction with the accompanying drawings:

FIG. 1: clevidipine degradation pathway.

DETAILED DESCRIPTION OF THE INVENTION

It is to be understood that the figures and descriptions of the present invention have been simplified to illustrate elements that are relevant for a clear understanding of the present invention, while eliminating, for the purpose of clarity, many other elements found in typical pharmaceutical compositions and methods of stabilization. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

As used herein, the term "clevidipine" shall mean and include all varieties or forms of clevidipine. Unless otherwise specified, examples of such forms include all pharmaceutically acceptable salts, esters, isomers, stereo isomers, crystalline and amorphous forms. One particular example is clevidipine butyrate. The amount of clevidipine in the formulations of the present invention can vary depending on the total overall volume of the formulation and the concentration of the other components. However, the amount of clevidipine in the formulation will generally range from about 0.005 to about 1.0% w/v, and includes ranges of from about 0.03 to about 0.5% w/v, and from about 0.01 to about 1.0% w/v. In particular embodiments, the amount of clevidipine in the formulation will be about 0.05, 0.1, or 0.3% w/v.

As used herein, the term "pharmaceutically acceptable salt" shall refer to salts prepared from pharmaceutically acceptable non-toxic bases or acids including inorganic or organic bases and inorganic or organic acids. Examples of salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glutamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

As used herein, the term "pharmaceutically acceptable ester" shall refer to esters prepared by reaction of an oxo-acid with a compound containing a hydroxyl group. Generally esters are derived from an inorganic or organic acid and an alcohol. More commonly esters are prepared by condensing an organic acid and an alcohol. Examples of suitable esters that may be used in the formulations of the present invention include butyric acid esters, such as those prepared in accordance with teachings in U.S. Pat. Nos. 5,856,346, 5,739,152, 6,350,877 and the like.

Clevidipine is manufactured by reaction of 4-(2',3'-dichlorophenyl)-1,4-dihydro-5-methoxycarbonyl-2,6-dimethyl-3-pyridinecarboxylic acid with chloromethyl butyrate to obtain clevidipine. This reaction can be done optionally in the presence of a corresponding hydrogen carbonate, such as $KHCO_3$, in refluxing acetonitrile. Inorganic salts can be removed by filtration and the product is crystallized by the addition of isopropanol and water with subsequent cooling. It can also be crystallized by exchanging solvent from acetonitrile to a mixture of alcohol, such as ethanol or isopropanol, and water with repeated evaporations. In the further purification of the product the crystals are washed with a mixture of water and ethanol or isopropanol. The product can be dissolved in refluxing isopropanol, crystallized by cooling, isolated by filtration and finally washed with a water and isopropanol mixture. A more detailed description of the manufacturing process of clevidipine can be found in U.S. Pat. No. 6,350,877, the entire disclosure of which is incorporated by reference herein as if set forth in its entirety. As used herein, the range of clevidipine that may be used in the formulations includes a range of from about 0.005% to about 1% w/v.

Compositions containing clevidipine as an active ingredient are sensitive to water, heat, and light. Clevidipine degrades under adverse conditions into several impurities that compromise the potency of clevidipine. A degradation pathway of clevidipine is shown in FIG. 1. This pathway identifies a number of clevidipine degradation products, including for example, H152/81, H168/79, H207/59, H324/78 and H152/66.

As with any of the exemplary embodiments of pharmaceutical compositions described herein, it is preferred that the level of clevidipine impurities in the composition is as low as possible. Therefore, while various exemplary embodiments of pharmaceutical compositions include levels of impurities within acceptable and effective ranges for the compositions as a whole, the more pure the composition, the more desirable the composition. The amount of clevidipine degradation products present in the formulations of the present invention is less than about 5%, 3%, 2%, 1%, 0.9%, 0.8%, 0.7%, 0.6%, 0.5%, 0.4%, 0.3%, or 0.2%, or even less.

The pharmaceutical formulations of the present invention are emulsion formulations. For compounds that have poor solubility and stability in water, emulsions offer much better solubility, and stability than conventional aqueous solutions. Oil-in-water emulsions also prevent the compound from adherence to plastic infusion sets that are to be used when administering the compound. Further information regarding the formulation of clevidipine can be found in U.S. Pat. No. 5,739,152, the entire disclosure of which is incorporated by reference herein as if set forth in its entirety.

As used herein, the term "antimicrobial agent" means an agent that inhibits the growth of microorganisms such as bacteria and fungi (molds and yeast). Particular classes of antimicrobial agents include chelating agents and alcohols. Chelating agents include, but are not limited to, ethylenediamine tetraacetic acid (EDTA) and salts thereof, citric acid and salts there of, and the like. Exemplary chelating agents are disodium edetate and sodium citrate. Alcohols include, but are not limited to, benzyl alcohol and chlorobutanol. Representative antimicrobial agents include EDTA, ascorbic acid, BHA/BHT, benzyl alcohol, benzoic acid, citric acid, edetic acid, parabens, phenol, propyl gallate, sorbic acid, sodium bisulfite, sodium sulfite, benzoic acid, chlorobutanol, chlorocresol, cresol, dehydroacetic acid, phenol, potassium benzoate, potassium sorbate, sodium benzoate, sodium dehydroacetate, sodium propionate, sorbic acid, thymol, benzalkonium chloride, benzethonium chloride, butyl paraben, cetylpyridinium chloride, ethylparaben, methylparaben, methylparaben sodium, propylparaben, propylparaben sodium, chlorocresol, cresol, dehydroacetic acid, ethylparaben, methylparaben, methylparaben sodium, phenol, potassium sorbate, thimersol and the various salt forms for these compounds.

In general the term "EDTA" means ethylenediamine tetraacetic acid and its derivatives and salts thereof. Particular derivative of use in the present invention includes disodium edetate. The nature of the EDTA derivative or salt is not critical, provided that it inhibits growth of microorganisms in the formulations of the present invention.

The amount of antimicrobial agent in the formulations of the present invention can vary depending on the total overall volume of the formulation and the concentration of the other components. However, the amount of the antimicrobial agent in the formulation will generally range from about 0.001 to about 1.5% w/v, and includes from about 0.005 to about 0.5% w/v, from about 0.001 to about 0.1% w/v, from about 0.01 to about 0.1% w/v, and from about 0.1 to about 1% w/v. In particular embodiments, the amount of the antimicrobial agent in the formulation will be about 0.1, 0.2, or 0.4% w/v. Where a chelating agent is used as the antimicrobial agent, the amount of chelating agent in the formulation will generally range from about 0.001% to about 0.5% w/v. The antimicrobial agent may comprise one, or more than one agent, such as two, three, four, etc., different antimicrobial agents.

As used herein, the term "antioxidant" in the formulations includes sodium ascorbate, cysteine hydrochloride, sodium bisulfite, sodium metabisulfite, sodium sulfite, ascorbyl palmitate, butylated hydroxyanisole (BHA), butylated hydroxytoluene (BHT), propyl gallate, tocopherol, and their pharmaceutically acceptable salts. An exemplary antioxidant is sodium ascorbate. The amount of antioxidant in the formulations of the present invention can vary depending on the total overall volume of the formulation and the concentration of the other components. However, the amount of the antioxidant in the formulation will generally range from about 0.01 to about 1.0% w/v, and includes from about 0.05 to about 1.0% w/v, and from about 0.05 to about 0.5% w/v. In particular embodiments, the amount of antioxidant in the formulation will be about 0.1% w/v.

As used herein, the term "lipid" in the formulations is any pharmaceutically acceptable oil, preferably a triglyceride such as soybean oil, safflower seed oil, olive oil, cottonseed oil, sunflower oil, sesame oil, peanut oil, corn oil, a medium chain triglyceride (such as Miglyol™ 812 or 810) or triacetin. The lipid may also be a propylene glycol diester or monoglyceride (such as acetylareal monoglyceride). The lipid can also be a mixture of one or more of these lipids. An exemplary lipid is soybean oil. The amount of lipid in the formulations of the present invention can vary depending on the total overall volume of the formulation and the concentration of the other components. However, the amount of lipid in the formulation will generally range from about 2 to about 30% w/v, and includes from about 5 to about 30% w/v, and from about 10% to about 20% w/v. In particular embodiments, the amount of lipid in the formulation will be about 20% w/v.

As used herein, the term "emulsifier" represents suitable pharmaceutically acceptable surfactants used in the formulations, preferably naturally occurring phospholipids extracted from egg yolk or soy bean, synthetic phosphatidyl cholines or purified phosphatidyl cholines from vegetable origin. Hydrogenated derivatives can also be used, such as phosphatidyl choline hydrogenated (egg) and phosphatidyl choline hydrogenated (soya). The amount of phospholipid emulsifier in the formulations of the present invention can vary depending on the total overall volume of the formulation and the concentration of the other components. However, the amount of emulsifier in the formulation will generally range from about 0.2 to about 2.0% w/v, and includes from about 0.5 to about 1.5% w/v. In particular embodiments, the amount of emulsifier in the formulation will be about 1.2% w/v.

As used herein, the term "co-emulsifier" represents a second pharmaceutically acceptable surfactant that may be included in the formulations of the invention. Such surfactants include synthetic nonionic surfactants such as poloxamers (for example Poloxamer 188 and 407), Cremophor™, poloxamines, polyoxyethylene stearates, polyoxyethylene sorbitan fatty acid esters or sorbitan fatty acid esters, derivatives of tocopherol such as tocopherol PEG succinate, long chain fatty acids such as oleic acid, stearic acid, palmitic acid, bile acids such as cholic acid and deoxycholic acid or surface active derivatives, and pharmaceutically acceptable salts thereof. An exemplary surfactant is oleic acid. The amount of co-emulsifier in the formulations of the present invention, when present, can vary depending on the total overall volume of the formulation and the concentration of the other components. However, the amount of surfactant in the formulation will generally range from about 0.005 to about 2% w/v, and includes from about 0.01 to about 2% w/v, and from about 0.01 to about 1.0% w/v. In particular embodiments, the amount of surfactant in the formulation will be about 0.03% w/v.

As used herein, the term "tonicity modifier" in the formulations of the present invention includes sodium chloride, potassium chloride, mannitol, sucrose, lactose, fructose, maltose, dextrose, dextrose anhydrous, propylene glycol, glycerol and glycerin. An exemplary tonicity modifier is glycerin. The amount of tonicity modifier in the formulations of the present invention can vary depending on the total overall volume of the formulation and the concentration of the other components. However, the amount of tonicity modifier in the formulation will generally range from about 2 to about 3% w/v, and includes from about 2 to about 2.75% w/v. In particular embodiments, the amount of tonicity modifier in the formulation will be about 2.25% w/v. The terms "tonicity modifier" and "isotonicity adjuster" are used herein interchangably.

The amount of water in the formulations of the present invention, such as water-for-injections, is used to make up the volume to 100% w/v and can vary depending on the total overall volume of the formulation and the concentration of the other components.

As the formulations are intended for parenteral administration, the skilled artisan will understand that one or more additional components used in parenteral formulations may be included. Such additional components include stabilizing agents (e.g. carbohydrates, amino acids and polysorbates, such as 5% dextrose), solubilizing agents (e.g. cetrimide, sodium docusate, glyceryl monooleate, polyvinylpyrolidone (PVP) and polyethylene glycol (PEG), buffers (e.g. acetates, citrates, phosphates, tartrates, lactates, succinates, amino acids and the like), preservatives (e.g. BHA, BHT, gentisic acids, vitamin E, ascorbic acid, sodium ascorbate and sulfur containing agents such as sulfites, bisulfites, metabisulfites, thioglycerols, thioglycolates and the like), suspending or viscosity agents, chelating agents, and administration aids (e.g. local anesthetics, anti-inflammatory agents, anti-clotting agents, vaso-constrictors for prolongation and agents that increase tissue permeability).

Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of drug formulations can be used to effect such administration.

In intravenous use, a sterile formulation of the present invention can be dissolved or suspended in any of the commonly used sterile intravenous fluids and administered by infusion. Intravenous fluids include, without limitation, physiological saline, phosphate buffered saline, 5% dextrose in water or Ringer's™ solution. The parenteral dosage form of formulations of the present invention can also be a ready-to-use solution in sterile sealed vials, hermetically sealed ampoules or in sterile pre-filled syringes, for example.

The sterile pre-filled syringes are syringes that contain a unit dose of a pharmaceutical formulation of the present invention. Suitable syringes are widely available and well known to the skilled artisan. An exemplary sterile pre-filled syringe is one that has been loaded with a unit dose of the pharmaceutical formulation and that is enclosed in an opaque, sealed package from which oxygen has been excluded. For example, oxygen may be displaced with $CO_2$ and/or $N_2$.

The pharmaceutical formulations of the present invention will have a pH that ranges from about 6.0 to about 8.8. In particular embodiments, the pH ranges from about 6.5 to about 8.0. In particular embodiments, the pH is 6.2, 6.5, 6.75, 7.0, or 7.5. Bases such as NaOH, KOH, and $Ca(OH)_2$ may be used to achieve the desired pH.

As used herein, the terms "inhibit", "inhibiting" and "inhibition" have their ordinary and customary meanings, and include inhibiting the growth of a bacteria or fungus in the formulations of the present invention. Such inhibition may be described as no more than about 10 fold growth for at least 24 hours following a low level (1-1000 Cfu/mL) of extrinsic contamination. Such growth may be determined, for example, by determining the number of colony forming units in the formulation when cultured at room temperature.

The duration of time over which inhibition of microbial growth is maintained will vary depending on the environmental conditions to which the formulation is exposed, e.g., the conditions under which a sterile vial of the formulation is pierced by a needle or sterility is otherwise breached. However, in one embodiment of the invention, microbial growth is inhibited for at least about 24 or more hours after the formulation is exposed to low level extrinsic microbial contamination.

The skilled artisan will understand that the pharmaceutical formulations of the present invention may be prepared using art-accepted means for preparing emulsion formulations. A general procedure for preparing clevidipine formulations is described as follows: an oil phase containing soybean oil, clevidipine and egg yolk phospholipids is mixed with an aqueous phase containing glycerin, at approximately 70° C. to form a coarse emulsion. The pH of the coarse emulsion is adjusted using sodium hydroxide. Following pH adjustment, the coarse emulsion is homogenized under high pressure to produce a fine particle size and thus a stable emulsion. The emulsion is filled into appropriate containers and sterilized in an autoclave.

The invention is described in greater detail by reference to the following non-limiting examples.

EXAMPLES 1-5

Example 1

Formulations containing antimicrobial agents as shown in Table 1 below were are prepared by adding stock solutions of anti microbial agent at appropriate concentration to clevidipine emulsions.

TABLE 1

| | | (% w/v) | | | | |
|---|---|---|---|---|---|---|
| Function | | Example 1 | Example 2 | Example 3 | Example 4 | Example 5 |
| Active ingredient | Clevidipine butyrate | 0.05 | 0.05 | 0.05 | 0.05 | 0.05 |
| Oil phase | Soybean oil | 20 | 20 | 20 | 20 | 20 |
| Isotonicity adjuster | Glycerin | 2.25 | 2.25 | 2.25 | 2.25 | 2.25 |
| Microbial Growth Retardant | Disodium Edetate | 0 | 0.005 | 0.01 | 0 | 0.005 |
| Microbial Growth Retardant | Benzyl Alcohol | 0 | 0 | 0 | 0.4 | 0.1 |
| Emulsifier | Purified egg yolk phospholipids | 1.2 | 1.2 | 1.2 | 1.2 | 1.2 |
| pH adjuster | Sodium hydroxide | q.s | q.s | q.s | q.s | q.s |
| Aqueous Phase | Water for Injection | q.s to 100% | q.s to 100% | q.s to 100% | q.s to 100% | q.s to 100% |

Sterile clevidipine oil-in-water compositions prepared as described above were evaluated for microbial growth. Microbial growth inhibition was tested using standard UPS test organisms. Each formulation was tested against five standard USP test organisms: S. aureus (SA, ATCC #6538), P. aeruginosa (PA, ATCC #9027), E. coli (EC, ATCC #8739), C. albicans (CA, ATCC #10231), and A. niger (AN, ATCC #16404). Formulations were inoculated with suspensions of each organism in an amount that recovers less than 100 CFU (colony forming units) per filter. Inoculations for each formulation were conducted in triplicate.

Test samples were stored at 20-25° C. for the duration of the study. Testing was performed at Time 0, 24, and 48 hours after inoculation. At appropriate time points, the samples were filtered through a 0.45 micrometer membrane filter and washed with 0.1% sterile peptone solution to remove the preservatives for the purpose of recovering the microorganisms. The washed filters were aseptically removed and placed on appropriate microbiological growth medium.

S. aureus, P. aeruginosa and E. coli were plated on tripticase soy agar and incubated aerobically at 30-35° C. for 2 days or until countable colonies were formed, whichever occurred first. C. albicans and A. niger were plated on sabouraud dextrose agar and aerobically incubated at 20-25° C. for 7 days or until countable colonies were formed, whichever occurred first.

Microbial inhibition was considered acceptable if there was a delay in onset or retardation of growth such that there was less than 10-fold (1 log) increase in viable colonies over a 24-hour period.

The effectiveness of EDTA alone or in combination with benzyl alcohol on in microbial inhibition over a 24 hour period is demonstrated in Table 2 below. From these experiments it can be concluded that the presence of EDTA and benzyl alcohol either alone or in combination demonstrated microbial retardation capabilities.

TABLE 2

| Formulation | Microbial Retardant (% w/v) | Time Point | EC | SA | PA | CA | AN |
|---|---|---|---|---|---|---|---|
| Example 1 | None | 0 | 21 | 32 | 7 | 29 | 14 |
|  |  | 24 hours | TNTC | >300 | 210 | TNTC | 19 |
|  |  | 48 hours | C | TNTC | C | C | 35 |
| Example 2 | 0.005% EDTA | 0 | 30 | 24 | 11 | 35 | 36 |
|  |  | 24 hours | 2 | 21 | 2 | 233 | 30 |
|  |  | 48 hours | 0.3 | 14 | 5 | 310 | 25 |
| Example 3 | 0.01% EDTA | 0 | 23 | 5 | 5 | 20 | 31 |
|  |  | 24 hours | 4 | 15 | 0.1 | 77 | 17 |
|  |  | 48 hours | 3 | 16 | 0 | 250 | 40 |
| Example 4 | 0.4% Benzyl Alcohol | 0 | 26 | 21 | 17 | 22 | 16 |
|  |  | 24 hours | 63 | 34 | 2 | 45 | 19 |
|  |  | 48 hours | 102 | 66 | 1 | 910 | 37 |
| Example 5 | 0.1% Benzyl Alcohol/ 0.005% EDTA | 0 | 26 | 19 | 15 | 34 | 38 |
|  |  | 24 hours | 0.3 | 10 | 0.3 | 300 | 36 |
|  |  | 48 hours | 2 | 5 | 0 | 370 | 51 |

TNTC = too numerous to count
C = Confluent growth

Example 2

Formulations containing antimicrobial agents as shown in Table 3 below were prepared by adding stock solutions of anti microbial agent at appropriate concentration to clevidipine emulsions.

TABLE 3

| | | (% w/v) | |
|---|---|---|---|
| Function | | Example 6 | Example 7 |
| Active ingredient | Clevidipine butyrate | 0.05 | 0.05 |
| Oil phase | Soybean oil | 20 | 20 |
| Isotonicity adjuster | Glycerin | 2.25 | 2.25 |
| Microbial Growth Retardant | Disodium Edetate | 0.005 | 0.005 |
| Microbial Growth Retardant | Sodium Citrate | 0.1 | 0 |
| Antioxidant | Sodium Ascorbate | 0 | 0.1 |
| Emulsifier | Purified egg yolk phospholipids | 1.2 | 1.2 |
| pH adjuster | Sodium hydroxide | q.s | q.s |
| Aqueous Phase | Water for Injection | q.s to 100% | q.s. to 100% |

Compositions described above were evaluated for microbial growth following the procedure described previously. The effectiveness of EDTA in combination with sodium citrate or sodium ascorbate in retarding microbial growth over a 24 hour period is demonstrated in Table 4 below. From these experiments it can be concluded that the presence of EDTA in combination with sodium citrate or sodium ascorbate demonstrated microbial retardation capabilities.

TABLE 4

| Formulation | Microbial Retardant (% w/v) | Time Point | EC | SA | PA | CA | AN |
|---|---|---|---|---|---|---|---|
| Example 1 | None | 0 | 21 | 32 | 7 | 29 | 14 |
|  |  | 24 hours | TNTC | >300 | 210 | TNTC | 19 |
|  |  | 48 hours | C | TNTC | C | C | 35 |
| Example 6 | 0.005% EDTA/ 0.1% Sodium Citrate | 0 | 19 | 14 | 9 | 25 | 31 |
|  |  | 24 hours | 2 | 5 | 4 | 55 | 39 |
|  |  | 48 hours | 0 | 3 | 23 | 85 | 34 |
| Example 7 | 0.005% EDTA/ 0.1% Sodium Ascorbate | 0 | 25 | 30 | 16 | 29 | 34 |
|  |  | 24 hours | 0 | 25 | 26 | 209 | 37 |
|  |  | 48 hours | 0 | 19 | 42 | 3 > 300 | 45 |

TNTC = too numerous to count
C = Confluent growth

Example 3

Clevidipine emulsion formulations were exposed to high intensity light (combination of cool white fluorescent and near UV light) in an effort to demonstrate the impact of light on the chemical stability and the results are shown in Table 5 below:

TABLE 5

| Formulation | Microbial Retardant (% w/v) | Antioxidant (% w/v) | Oxidative Degradants Light Exposure (1.2 Million Lux Hours) | |
|---|---|---|---|---|
| | | | H324/78 | H152/66 |
| Example 1 | None | None | 0.2 | 0.4 |
| Example 2 | 0.005% EDTA | None | 0.2 | 0.2 |
| Example 7 | 0.005% EDTA | 0.1% Sodium Ascorbate | <0.1 | Not Detected |

It was unexpectedly found that the addition of ascorbic acid in the presence of EDTA was effective in inhibition of photodegradation of clevidipine in the emulsion, without counteracting the antimicrobial effectiveness of EDTA.

Example 4

Clevidipine emulsion formulations with EDTA alone or in combination with sodium citrate were prepared by adding EDTA and/or sodium citrate as a part of the emulsion process in order to confirm the antimicrobial characteristics previously observed when added as a solution to a prepared emulsion. The emulsion formulations shown below were prepared as follows: The oil phase containing soybean oil and egg yolk phospholipids was mixed with the aqueous phase containing glycerin, disodium edetate with or without sodium citrate and water at approximately 70° C. to form a coarse emulsion. The pH of the coarse emulsion was adjusted using sodium hydroxide. Following pH adjustment, the coarse emulsion was homogenized under high pressure to produce a fine particle size and thus a stable emulsion. The emulsion was filled into appropriate containers and sterilized in an autoclave.

These formulations were evaluated for microbial growth inhibition and the results are shown in Table 6 below.

TABLE 6

| Formulation | Microbial Retardant (% w/v) | Time Point | EC | SA | PA | CA | AN |
|---|---|---|---|---|---|---|---|
| Example 2 | 0.005% EDTA | 0 | 25 | 37 | 27 | 24 | 37 |
| | | 24 hours | 1 | 30 | 2 | 75 | 44 |
| | | 48 hours | 1 | 22 | 1 | 99 | 50 |
| Example 8 | 0.025% EDTA | 0 | 29 | 42 | 23 | 26 | 35 |
| | | 24 hours | 1 | 38 | 1 | 82 | 32 |
| | | 48 hours | 1 | 26 | 2 | 112 | 30 |
| Example 9 | 0.001% EDTA | 0 | 29 | 41 | 15 | 29 | 40 |
| | | 24 hours | 2 | 42 | 0 | 115 | 39 |
| | | 48 hours | 1 | 26 | 0 | 133 | 39 |
| Example 10 | 0.0025% EDTA/ 0.02% Sodium Citrate | 0 | 30 | 45 | 7 | 29 | 38 |
| | | 24 hours | 2 | 32 | 2 | 68 | 37 |
| | | 48 hours | 1 | 29 | 0 | 85 | 88 |
| Example 11 | 0.001% EDTA/ 0.02% Sodium Citrate | 0 | 26 | 32 | 29 | 22 | 40 |
| | | 24 hours | 1 | 39 | 0 | 64 | 41 |
| | | 48 hours | 1 | 26 | 7 | 40 | 41 |

The results demonstrate that varying concentrations of EDTA either alone or in combination with sodium citrate were effective in retarding microbial growth when added as a part of the manufacturing process.

Example 5

The physical stability of emulsions with anti microbial agents was evaluated via zeta potential measurement. The zeta potential, which is a measure of charge around the oil droplet, was determined to evaluate the physical stability of emulsion formulations containing antimicrobial agents. A larger absolute value of zeta potential results in increased electrostatic repulsion between oil droplets and is indicative of enhanced physical stability. The results demonstrated that the absolute value of zeta potential decreased in presence of EDTA alone or in combination with sodium citrate which was surprising given that their concentrations were low.

In an attempt to improve the physical stability of emulsions, use of oleic acid a co-emulsifier was investigated. Clevidipine emulsion with oleic acid as shown in the example below was manufactured using the following process: The oil phase containing soybean oil, clevidipine, egg yolk phospholipids and oleic acid was mixed with the aqueous phase containing glycerin, disodium edetate and water at approximately 70° C. to form a coarse emulsion. The pH of the coarse emulsion was adjusted using sodium hydroxide. Following pH adjustment, the coarse emulsion was homogenized under high pressure to produce a fine particle size and thus a stable emulsion. The emulsion was filled into appropriate containers and sterilized in an autoclave.

TABLE 7

| Function | | % w/v Example 12 |
|---|---|---|
| Active ingredient | Clevidipine butyrate | 0.05 |
| Oil phase | Soybean oil | 20 |
| Isotonicity adjuster | Glycerin | 2.25 |
| Microbial Growth Retardant | Disodium Edetate | 0.005 |
| Coemulsifier | Oleic acid | 0.03 |
| Emulsifier | Purified egg yolk phospholipids | 1.2 |
| pH adjuster | Sodium hydroxide | qs |
| Aqueous Phase | Water for Injection | qs to 100% |

The above composition was evaluated for zeta potential and microbial growth inhibition.

Inhibition of microbial growth for Example 12 is shown in Table 8 below for 12, 24, and 30 hours.

TABLE 8

| | CFU/5 mL | | | |
|---|---|---|---|---|
| Challenge Organism | 0 Hours | 12 Hours | 24 Hours | 30 Hours |
| S. marsacens (SM) | 29 | 32 | 32 | 40 |
| Staph. epidermidis (SE) | 30 | 6 | 5 | 5 |

The results for zeta potential are shown in Table 9 below and demonstrate that inclusion of oleic acid at a low concentration unexpectedly showed a substantial increase in zeta potential and physical stability of the emulsion compared to emulsions comprising EDTA alone or in combination with sodium citrate.

TABLE 9

| Formulation | Microbial Retardant (% w/v) | Co-emulsifier (% w/v) | Zeta Potential (mV) | pH |
|---|---|---|---|---|
| Example 1 | None | None | −25.6 | 7.7 |
| Example 2 | 0.005% EDTA (Lab scale) | None | −24.8 | 7.7 |
| Example 2 | 0.005% EDTA (pilot scale) | None | −17.6 | 7.7 |

TABLE 9-continued

| Formulation | Microbial Retardant (% w/v) | Co-emulsifier (% w/v) | Zeta Potential (mV) | pH |
|---|---|---|---|---|
| Example 11 | 0.001% EDTA/ 0.02% SC | None | −18.3 | 7.4 |
| Example 12 | 0.005% EDTA | 0.03% Oleic acid | −36.1 | 8.0 |

In addition as demonstrated in Table 10 below, oleic acid did not impact the antimicrobial effectiveness of EDTA.

TABLE 10

| Formulation | Microbial Retardant (% w/v) | Time Point | EC | SA | PA | CA | AN |
|---|---|---|---|---|---|---|---|
| Example 2 | 0.005% EDTA | 0 | 25 | 37 | 27 | 24 | 37 |
|  |  | 24 hours | 1 | 30 | 2 | 75 | 44 |
|  |  | 48 hours | 1 | 22 | 1 | 99 | 50 |
| Example 11 | 0.005% EDTA/ 0.03% Oleic Acid | 0 | 39 | 32 | 35 | 70 | 50 |
|  |  | 24 hours | 1 | 49 | 49 | 305 | 75 |
|  |  | 48 hours | 0 | 41 | 70 | 395 | 40 |

The invention claimed is:

1. A pharmaceutical formulation comprising,
(a) clevidipine butyrate, present at about 0.01 to about 1% w/v,
(b) EDTA, present at about 0.001 to about 0.1% w/v,
(c) soybean oil, present at about 4 to about 30% w/v,
(d) purified egg yolk phospholipids, present at about 0.2 to about 2% w/v,
(e) glycerin, present at about 2 to about 3% w/v, and
(f) water up to 100%.

2. The pharmaceutical formulation of claim 1, wherein the formulation has a pH of about 6 to about 8.8.

3. A pharmaceutical formulation comprising,
(a) clevidipine butyrate, present at about 0.01 to about 1% w/v,
(b) EDTA, present at about 0.001 to about 0.1% w/v,
(c) soybean oil, present at about 4 to about 30% w/v,
(d) purified egg yolk phospholipids, present at about 0.2 to about 2% w/v,
(e) sodium citrate, present at about 0.005 to about 0.5% w/v,
(f) glycerin, present at about 2 to about 3% w/v, and
(g) water to 100% w/v.

4. The pharmaceutical formulation of claim 3, wherein the formulation has a pH of about 6 to about 8.8.

5. A pharmaceutical formulation comprising,
(a) clevidipine butyrate, present at about 0.01 to about 1% w/v,
(b) EDTA, present at about 0.001 to about 0.1% w/v,
(c) soybean oil, present at about 4 to about 30% w/v,
(d) purified egg yolk phospholipids, present at about 0.2 to about 2% w/v,
(e) sodium ascorbate, present at about 0.01 to about 1% w/v,
(f) glycerin, present at about 2 to about 3% w/v, and
(g) water, to 100%% w/v.

6. The pharmaceutical formulation of claim 5, wherein the formulation has a pH of about 6 to about 8.8.

7. A pharmaceutical formulation comprising,
(a) clevidipine butyrate, present at about 0.01 to about 1% w/v,
(b) EDTA, present at about 0.001 to about 0.1% w/v,
(c) oleic acid, present at about 0.01 to about 2.0% w/v,
(d) soybean oil, present at about 4 to about 30% w/v,
(e) purified egg yolk phospholipids, present at about 0.2 to about 2% w/v,
(f) glycerin, present at about 2 to about 3% w/v, and
(g) water, up to 100% w/v.

8. The pharmaceutical formulation of claim 7, wherein the formulation has a pH of about 6 to about 8.8.

9. A pharmaceutical formulation comprising,
(a) clevidipine butyrate, present at about 0.01 to about 1% w/v,
(b) EDTA, present at about 0.001 to about 0.1% w/v,
(c) oleic acid, present at about 0.01 to about 2.0% w/v,
(d) soybean oil, present at about 4 to about 30% w/v,
(e) purified egg yolk phospholipids, present at about 0.2 to about 2% w/v,
(f) sodium citrate, present at about 0.005 to about 0.5% w/v,
(g) glycerin, present at about 2 to about 3% w/v, and
(h) water, up to 100% w/v.

10. The pharmaceutical formulation of claim 9, wherein the formulation has a pH of about 6 to about 8.8.

11. A pharmaceutical formulation comprising,
(a) clevidipine butyrate, present at about 0.01 to about 1% w/v,
(b) EDTA, present at about 0.001 to about 0.1% w/v,
(c) oleic acid, present t about 0.01 to about 2% w/v,
(d) soybean oil, present at about 4 to about 30% w/v,
(e) purified egg yolk phospholipids, present at about 0.2 to about 2% w/v,
(f) sodium ascorbate, present at about 0.05 to about 1.0% w/v,
(g) glycerin, present at about 2 to about 3% w/v, and
(h) water, up to 100%.

12. The pharmaceutical formulation of claim 11, wherein the formulation has a pH of about 6 to about 8.5.

* * * * *